US010971256B2

(12) United States Patent
Stephenson

(10) Patent No.: US 10,971,256 B2
(45) Date of Patent: *Apr. 6, 2021

(54) SYSTEM AND METHOD FOR IMPROVING HEALTHCARE THROUGH SOCIAL ROBOTICS

(71) Applicant: Humana Inc., Louisville, KY (US)

(72) Inventor: Peter Stephenson, Miami Beach, FL (US)

(73) Assignee: Humana Inc., Louisville, KY (US)

( * ) Notice: Subject to any disclaimer, the term of this patent is extended or adjusted under 35 U.S.C. 154(b) by 88 days.

This patent is subject to a terminal disclaimer.

(21) Appl. No.: 16/227,773

(22) Filed: Dec. 20, 2018

(65) Prior Publication Data

US 2019/0122319 A1    Apr. 25, 2019

Related U.S. Application Data

(63) Continuation of application No. 12/711,585, filed on Feb. 24, 2010, now Pat. No. 10,163,175.

(60) Provisional application No. 61/155,391, filed on Feb. 25, 2009.

(51) Int. Cl.
*G16H 20/00* (2018.01)
*G16H 40/67* (2018.01)
*G06F 19/00* (2018.01)

(52) U.S. Cl.
CPC .............. *G16H 20/00* (2018.01); *G06F 19/00* (2013.01); *G16H 40/67* (2018.01)

(58) Field of Classification Search
CPC ........ G16H 10/00; G16H 10/40; G16H 15/00; G16H 20/00; G16H 20/10; G16H 20/13; G16H 20/17; G16H 30/00; G16H 40/00; G16H 50/00; G16H 70/00; G16H 80/00; G06Q 50/22; G06F 19/00
USPC .................................................. 705/2, 3, 20
See application file for complete search history.

(56) References Cited

U.S. PATENT DOCUMENTS

| 6,085,752 A | 7/2000 | Kehr et al. |
| 6,415,203 B1 | 7/2002 | Inoue et al. |
| 2005/0154265 A1 | 7/2005 | Miro et al. |
| 2005/0191716 A1 | 9/2005 | Surwit et al. |
| 2005/0216126 A1 | 9/2005 | Koselka et al. |
| 2006/0293787 A1 | 12/2006 | Kanda et al. |
| 2008/0004904 A1 | 1/2008 | Tran |
| 2008/0166945 A1 | 7/2008 | Cheng et al. |

*Primary Examiner* — Robert W Morgan
*Assistant Examiner* — Charles P Coleman
(74) *Attorney, Agent, or Firm* — Standley Law Group LLP

(57) ABSTRACT

A computerized system comprising a social robot for interacting with a patient in order to improve the patient's adherence to a health or medical regime. A patient is instructed to perform a health activity (e.g., take medication, step on scale, measure glucose, play a game) at certain intervals in order to reach a specified goal or expected result. The results of the health activity are recorded in a wireless health device and transmitted to a computer. The computer interprets the result of health activity and communicates an action to the robot. If the patient performs the activity within a specified interval and results are consistent with the specified goal or expected result, the robot communicates a positive reaction. If the patient does not perform the activity within a specified interval, or if the results are not consistent with the specified goal or expected result, the robot communicates a negative reaction.

20 Claims, 9 Drawing Sheets

SYSTEM AND METHOD FOR IMPROVING HEALTHCARE THROUGH SOCIAL ROBOTICS

CROSS REFERENCE TO RELATED APPLICATIONS

This application is a continuation of U.S. application Ser. No. 12/711,585 filed Feb. 24, 2010, which claims priority to U.S. Provisional Application Ser. No. 61/155,391 filed Feb. 25, 2009, the disclosures of each of which are hereby incorporated by reference in their entireties.

TECHNICAL FIELD

The present invention relates generally to healthcare programs. More particularly, exemplary embodiments relate to a system and method for assisting caregivers of the elderly through the introduction of a social robot which has been programmed to perform the roles of both a healthcare tool as well as a companion. The social robot may be capable of performing numerous functions and may provide an interface to technology that is more approachable for the elderly.

BACKGROUND AND SUMMARY OF THE INVENTION

As the aging baby boomer generation approaches retirement age, healthcare providers are searching for ways to ease the burden of an increasingly older population. Subsequent generations are migrating away from their parents and grandparents which significantly increases the relevance of assisted living facilities in the lives of elderly patients. Moreover, a rising life expectancy and dependence on a greater number of health professionals is contributing to a more expensive healthcare system. Social robotics is a technology proposed to assist caregivers in menial tasks as well as extend the independence and quality of life for aging individuals.

A social robot is an autonomous robot that interacts and communicates with humans or other autonomous physical agents by following social behaviors and rules attached to its roles. The field of social robotics was started in the 1940s-1950s. Autonomy is a requirement for social robots. A completely remote controlled robot cannot be considered to be social because it does not make decisions by itself. In this vein, a remote-controlled robot is merely the extension of its human controller. This does not mean however that a robot must be completely autonomous to be considered a social robot. A robot with only partial autonomy is often times still considered to be social.

For many elderly patients, loneliness is a most serious condition. Many senior citizens have been left widowed and/or in a nursing home or other facility with no one to come and visit. Many of these individuals suffer physical ailments and set-backs due to a lack of social stimulation. Some institutions have recognized the benefits of domestically trained pets in these situations and provide such companions to their elderly patients. It has been concluded that pets can satisfy many of the needs of elderly patients and encourage them to hold on to the world of reality and of intense emotional relationships.

One object of the present invention is to simulate the type of social interactivity elderly patients receive through developing a relationship with a pet through a social robot that is capable of providing additional care-giving utilities. One exemplary embodiment of the present invention utilizes a robot, such as the PLEO™, previously manufactured by robotics developer UGOBE, as a platform for robotic technology. The robotic dinosaur is an autonomous social robot which imitates a baby Camarasauras maturing into a young adult. To perform exemplary embodiments of the system and method of the present invention, the robotic dinosaur, is reprogrammed to perform the roles of both a healthcare tool and companion. In many exemplary embodiments, the reprogrammed robotic dinosaur may provide an interface to technology that is more approachable to the elderly. Additional exemplary embodiments implement social robots other than a robotic dinosaur that have been programmed to exhibit the desired applications.

In exemplary embodiments of the system and method of the present invention, a social robot is programmed so that it is capable of socially interacting with an elderly patient in order to improve the patient's adherence to a health or medical regime. This interaction can be carried out in such a way that the relationship formed between the elderly patient and the social robot increases the likelihood of the patient taking his or her medication as scheduled. For example, in one exemplary embodiment where a reprogrammed robotic dinosaur is being utilized as the social robot interface, the robotic dinosaur may begin to exhibit symptoms of illness, discontent, etc., unless the elderly patient takes his or her medication as scheduled. Because the elderly patient has developed a relationship with the robotic dinosaur and cares for its wellbeing, the patient will take his medication to benefit his robotic dinosaur. In exemplary embodiments, an intended consequence of the relationship formed between the elderly patient and the social robot is the improved healthcare of the elderly patient. In other exemplary embodiments, the social robot may also be programmed to remind an elderly patient of important events as well as play games with the elderly patient. In a preferred exemplary embodiment, a social robot is capable of interacting with an elderly patient and performing a memory game.

In some exemplary embodiments, a social robot is at least partially controlled remotely by an application run on a computer. The computer may be equipped with programs which make possible the monitoring of various healthcare related statistics of an elderly patient. For example, the computer may have a program which monitors the patient's weight and is able to produce various graphs and figures depicting the patient's weight history. Some exemplary embodiments of the program keep track of a patient's weight goal and provide a healthcare provider with statistics related to their patient's progress in meeting that goal. If for example a given patient is under weight, the program may be capable of providing the healthcare provider with information relating to the average number of calories the patient has been consuming per day and how many additional calories should be added to the patient's diet to help the patient meet his or her ideal weight.

In one exemplary embodiment where a social robot is controlled remotely by an application executing on a computer, the social robot acts as the primary interface to the elderly patient that assists in the collection of data utilized by the computer's application. In the exemplary embodiment where the computer program is able to monitor a patient's weight history, the social robot may be able to upload data from a scale which the patient uses to weigh him or her self. Additionally, the robot may be able to react to the data which it uploads in order to encourage the patient's compliance with a certain regimen. The regimen may include performing certain health activities at particular times or at particular frequencies in order to reach a particular health goal. For example, if a certain patient using the present system is overweight, the health activity may include regular weigh-ins (e.g., weekly, bi-weekly, etc.). The health goal may be a target weight. The patient may be encouraged to follow a special diet in order to lose weight. After performing the health activity (i.e., weigh-in), data uploaded into the robot from the patient's scale may indicate that the patient has gained weight since his or her last weigh-in. The robot may then respond to this result by conveying that it is disappointed. The patient is ideally encouraged to get back on his or her diet in order to receive a satisfied response from the robot at the next weigh-in. If the patient does not perform the health activity within an expected timeframe, the robot may be programmed to act in manner that serves as a reminder to the patient to perform the health activity. In preferred exemplary embodiments, data from a wireless healthcare device is not actually uploaded into the robot, but rather is uploaded directly into the computer which then sends a signal to the robot where the signal causes the robot to exhibit a certain behavior.

In some exemplary embodiments where a social robot is controlled remotely by an application executing on a computer, the application utilizes data relating to many different healthcare issues. For example, the application may utilize data relating to a patient's blood pressure, heart rate, sleep schedule, physical activity, etc. A regiment for performing health activities may be established for each of these health conditions. For example, a patient may be instructed to measure his or her blood pressure daily. Results are compared to a target to determine whether the patient is making progress toward a goal or within an expected or preferred range. In a preferred embodiment, a social robot is programmed to exhibit responses based on all the data recorded in the computer's application. The responses exhibited by the social robot based on the data recorded in the computer's application may de different for each data set, but this is not required.

BRIEF DESCRIPTION OF THE DRAWINGS

A better understanding of the disclosed embodiments will be obtained from a reading of the following detailed description and the accompanying drawings wherein identical reference characters refer to identical parts and in which.

DETAILED DESCRIPTION

Figure 1:
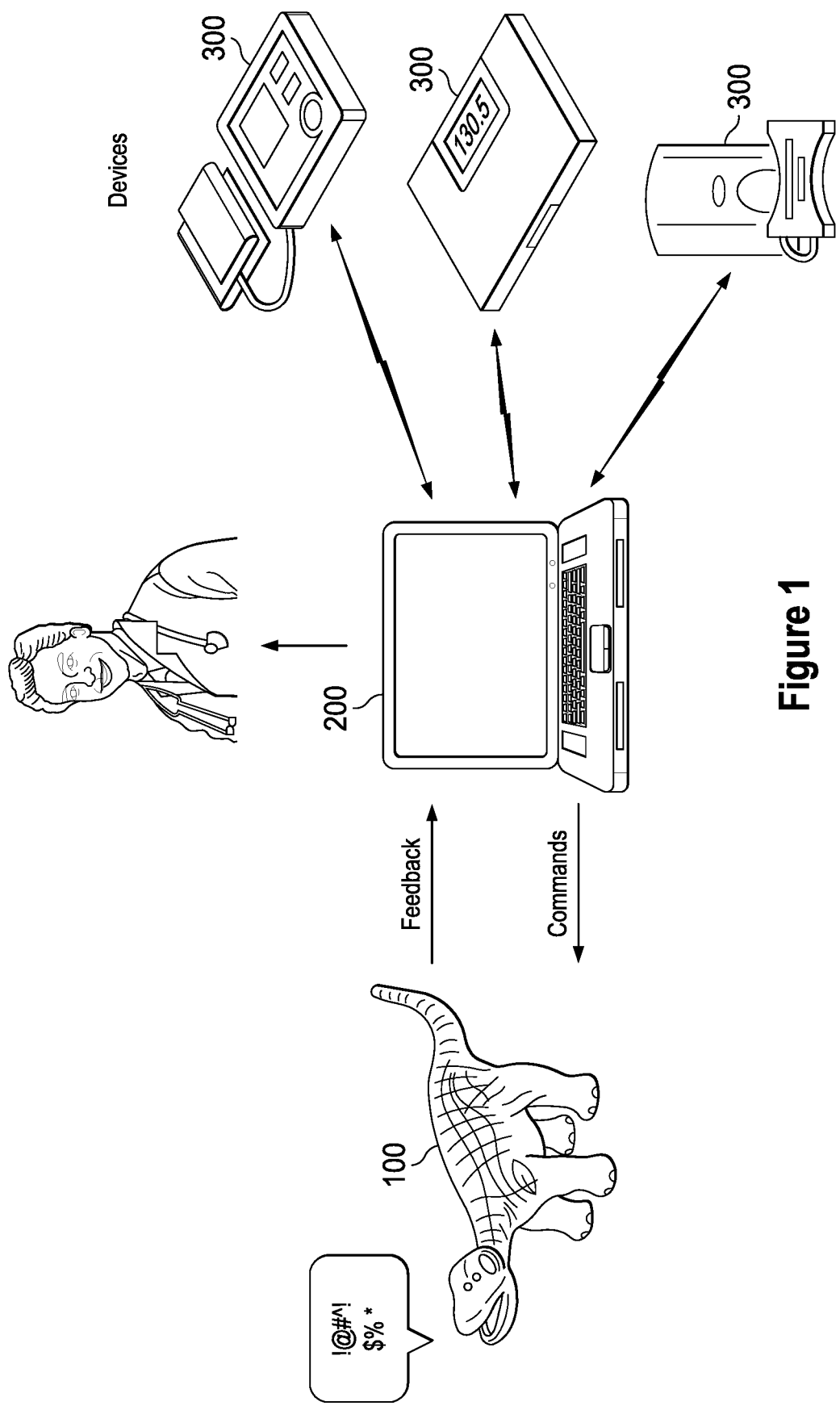
FIG. 1 shows a flow chart of an exemplary embodiment of the system and method of the present invention.

An exemplary embodiment of a system for improving healthcare through social robotics comprises a social robot, a computer, a program in the computer which enables communication between the computer and the robot, and a wireless healthcare device. In some exemplary embodiments, the computer program may also enable communication between the computer and the wireless healthcare device. The program in the computer may comprise code capable of handling communication with the social robot over serial/wireless connections. In a preferred exemplary embodiment, the computer receives data from the wireless electronic device where the data relates to a health activity of the patient, processes the data, and transmits a behavior cue to the robot based on the received data. FIG. 1 shows a flow chart for an exemplary embodiment of the system and method of the present invention where the system comprises an exemplary embodiment of a social robot 100, a computer 200, a program in the computer which enables communication between the computer 200 and the robot 100, and a wireless healthcare device 300. In a preferred exemplary embodiment, the program in the computer 200 is designed to be utilized by a system user who is the healthcare provider of an elderly patient. A patient interacting with a social robot 100 may also be considered a system user.

The social robot utilized by the present system and method may be the PLEO™, previously manufactured by robotics developer UGOBE. The PLEO is an autonomous social robot which imitates a baby Camarasauras maturing into a young adult. To perform an exemplary embodiment of the system and method of the present invention, the robotic dinosaur may be reprogrammed to perform the roles of both a healthcare tool and companion. In many exemplary embodiments, the reprogrammed robotic dinosaur may provide an interface to technology that is more approachable to the elderly. Additional exemplary embodiments implement social robots other than a robotic dinosaur.

In a preferred exemplary embodiment, a social robot interacts with an elderly patient in a manner which causes the patient to adhere to a health regime. A robot of the present system and method may interact with the patient in a manner that can, on some levels, be compared to the type of interaction an individual would have with a pet. For example, a robot could be programmed to show signs of affection towards a patient as well as to show signs that its survival depends on the well-being of the patient. Both of these behaviors when exhibited by a robot could in some instances encourage a patient to adhere to a health regime. For example, a robot could be programmed to exhibit signs of hunger if a patient with whom it is interacting does not eat according to a pre-determined meal plan. If the patient has grown to care about the robot, the patient may stick to his or her diet to ensure the robot does not exhibit signs of hunger. Similarly, a robot could be programmed to exhibit signs of illness if a patient does not take his or her medication according to a specific schedule—if the patient does not want to see the robot act ill, he or she may take the medication as required to prevent the robot from exhibiting this behavior.

In some exemplary embodiments, a robot may be programmed to show signs of approval or disapproval in response to certain behaviors exhibited by a patient. For example, if a patient is diabetic and is supposed to measure his or her blood glucose levels at certain times throughout the day, a robot may exhibit signs that it is pleased each time the patient takes a reading at the appropriate time. In contrast, a robot might shows signs that it is unhappy if a patient misses taking a measurement. There are many different signs of approval that a social robot could be programmed to exhibit including but not limited to the playing of a certain song, "smiling" at a patient, wagging a tail if it has one, etc. Signs of disapproval that could be exhibited by a robot comprise the making of certain sounds, contorting its shape in a certain manner, turning its back on the patient, etc. The signs exhibited by a robot can in some embodiments be tailored to meet the needs and/or personality of the patient (or patients) with whom the robot interacts.

Though robots do not have emotions, one embodiment of the system and method comprises programming which permits the robot to exhibit actions, sounds, signals, etc. which could leave an impression in the mind of a system user that the robot does in fact have emotions. In one preferred embodiment, a robot exhibits actions, sounds, signals, etc. that create the impression that it cares about a system user. In some instances where the system is being utilized by an elderly patient, the fact that a robot can exhibit actions, sounds, signals, etc. that create the impression that the robot cares about the patient, the patient begins to think of the robot as a friend and companion. The fact that the patient begins to think of the robot as a friend may permit the robot to more easily assist the role of healthcare provider.

In some exemplary embodiments, a social robot interacts with an individual and encourages him or her to take part in a certain behavior. In a preferred exemplary embodiment, the behavior requires utilization of a healthcare device. In some exemplary embodiments comprising a healthcare device, the healthcare device may be utilized to obtain data relating to a patient's health activity. For example, a robot may make a sound indicating that a patient needs to weigh himself with a scale. In one exemplary embodiment, the scale is in communication with the computer that is also in communication with the robot. In this exemplary embodiment, the scale could send an electronic message to the computer when the scale has recorded the weight of the individual. The message may comprise weight data as well as other data. Once the message has been received by the computer, the computer may send an electronic message to the robot which could cause the robot to exhibit a certain behavior. In a preferred exemplary embodiment, the message sent to the robot depends on whether or not the data received from the healthcare device complies with a patient's regimen data. Regimen data may be stored in a database of the computer, but in some exemplary embodiments comprising a database, the database may be located outside of the computer but can be accessed by the computer. In an exemplary embodiment where the health activity relates to a patient weighing himself, the behavior exhibited by the robot could be in response to the patient's weight that has been recorded by the scale, but it could also be in response to the fact that the individual weighed him or herself as scheduled (i.e., at a certain time). In exemplary embodiments comprising regimen data, a regimen may comprise patient goal data, healthy and unhealthy level data, schedule data, etc. In a preferred exemplary embodiment a given patient has more than one regimen where each regimen relates to a different health activity. In some embodiments, a robot may exhibit responses to multiple activities at the same time, in sequence, etc.

In a preferred exemplary embodiment, a social robot reacts to the use of at least one healthcare device. A scale, blood pressure cuff, thermometer, glucose meter, and urinalysis machine are just a few of the healthcare devices that may be implemented in practicing the present system and method. In some exemplary embodiments, a robot reacts to the healthcare device by receiving a signal from a computer that has electronically received data from the device. In a preferred exemplary embodiment, when a wireless electronic device of the system has been used to record a biometric measurement and the measurement falls within a healthy range, the robot with exhibit signs that it is healthy but when the measurement falls inside an unhealthy range the robot exhibits signs that it is unhealthy.

Some exemplary embodiments implement Bluetooth® technology. Put simply, Bluetooth is a short-range wireless radio technology that allows electronic devices to connect to one another. Generally, Bluetooth has a range of 30 ft. or greater depending on the Bluetooth Core Specification Version being utilized. Some devices have Bluetooth ranges in excess of 100 ft. Bluetooth devices utilize a radio broadcast system to communicate with one another thereby making it unnecessary for two devices to be in line sight of each other for data to be exchanged. In a preferred exemplary embodiment, a healthcare device is Bluetooth enabled and once the device has been used to collect data, it can then wirelessly transmit the data to another Bluetooth enabled device. In some embodiments utilizing Bluetooth technology, data is wirelessly transmitted straight from a healthcare device to the computer that is in communication with the social robot. In some exemplary embodiments, a healthcare device utilizes Bluetooth technology to send data to a computer other than the computer that is in communication with the social robot. In these exemplary embodiments, the computer in communication with the robot may later receive a signal from the computer communicating with the healthcare device that causes the robot to react to a measurement that has been taken with the healthcare device. In other exemplary embodiments, data may be transmitted from a healthcare device that utilizes Bluetooth technology to a mobile phone, PDA, health appliance, etc.

In some exemplary embodiments comprising Bluetooth technology, the system may further comprise a Bluetooth Service Module. In some embodiments, a Bluetooth Service Module is accessed through a Bluetooth Service frame. In an preferred exemplary embodiment, a Bluetooth Service Module permits AnD medical devices to be registered with the computer so that the application can detect AnD Bluetooth signals. In some embodiments, once a Bluetooth Service Module has enabled the detection of AnD Bluetooth signals that have originated from a medical device, the computer program can then access the signals in order to obtain medical data concerning a patient that has utilized the medical device. Medical data may comprise weight data, blood glucose level data, blood pressure data, etc.

In some exemplary embodiments of the present system, the system comprises a USB driver. In a preferred exemplary embodiment a USB driver consists of a NAND-type flash memory storage device integrated with a USB (Universal Serial Bus) interface. The USB driver may be both removable and rewritable. In some exemplary embodiments comprising a USB driver, the driver is plugged into a port on the computer prior to operating a social robot. In other exemplary embodiments, the USB driver is not plugged into the computer prior to utilizing a social robot, but rather it is plugged into the computer prior to running a certain application with the social robot. In a preferred exemplary embodiment, plugging the USB driver into a port on the computer enables communication between the computer and a social robot.

Figure 2:
FIG. 2 shows a screenshot of an exemplary embodiment of the software interface of the system and method of the present invention wherein three different exemplary embodiments of frames are shown.

In some exemplary embodiments, the system and method of the present invention comprises a computer program. The computer program may be written in JAVA. In other exemplary embodiments, the computer program is written utilizing a software platform other than JAVA. In a preferred exemplary embodiment, a computer program creates a "robot interface." The robot interface may comprise a display on a computer screen which contains information pertaining to data that has been received by the computer from the robot. The robot interface may also permit system users to instruct the computer program to cause certain data to be sent to the robot. In a preferred exemplary embodiment, the present system and method comprises a robot-interface with multiple frames. FIG. 2 shows a screenshot of an exemplary embodiment of a robot interface of the system and method of the present invention wherein three different exemplary embodiments of frames 400, 402, 404 are shown. In one exemplary embodiment at least one frame within the robot interface provides access to a module (i.e., an application) of the system. As shown in FIG. 2, exemplary frames 400 and 402 each provide access to a module (the daily schedule module and the skit player module respectively). In another exemplary embodiment, a single frame within the robot-interface may provide access to more than one module.

Figure 3:
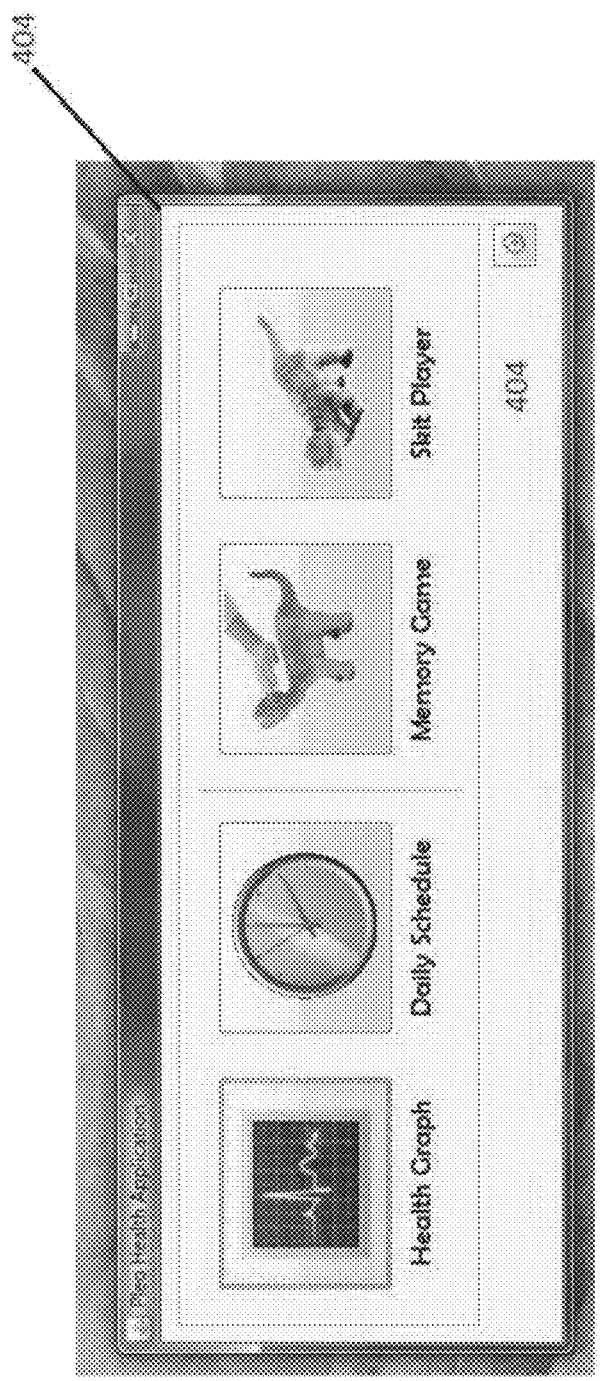
FIG. 3 shows a screenshot of an exemplary embodiment of a main frame.

In a preferred exemplary embodiment, the present system and method may comprise a robot-interface with a "main frame." In the exemplary embodiment of FIG. 2, an exemplary main frame 404 is shown. The main frame 404 may be titled the "Robot Health Application." In an exemplary embodiment where the social robot comprises a robotic dinosaur, the main frame 404 may be titled "Health Application." FIG. 3 shows a screen shot of an exemplary embodiment of a main frame 404 titled "Health Application." There are countless titles that could be given to a main frame 404. In an exemplary embodiment comprising a main frame 404, a user of the present system and method may access the main frame 404 in order to select the applications that he or she chooses to run with the social robot. In the exemplary main frame 404 shown in FIG. 3, it may be utilized to access the health graph, daily schedule, memory game, and skit player applications. In a preferred exemplary embodiment, selecting an application within the main frame 404 causes a new frame to be opened for the selected application. In other exemplary embodiments, the main frame 404 also provides access to healthcare applications that do not necessarily implement the social robot. It is also possible that the main frame 404 provides access to other computer programs that are not healthcare applications such as Microsoft Word, Microsoft Excel, email, etc.

In a preferred exemplary embodiment, the main frame 404 is the access point to all of the system's applications. In some exemplary embodiments, when the main frame 404 is closed, all of the system's frames are automatically closed and therefore access to the system's applications cannot be had until the main frame 404 is reopened. In other exemplary embodiments, the system can be configured such that closing the main frame 404 does not prevent access to all of the system's applications.

In a preferred exemplary embodiment where the present system and method comprise a robot-interface that comprises a main frame 404, the main frame 404 may provide access to some or all of the following applications: device manager; event scheduler; graphical user interface; Bluetooth service module; health graph; skit player; medication regimen; memory game; weight program; and blood pressure program. In another exemplary embodiment, the main frame 404 may provide access to applications other than those listed. In yet another exemplary embodiment, some or all of these applications may be accessible from a frame other than a main frame 404.

Figure 8:
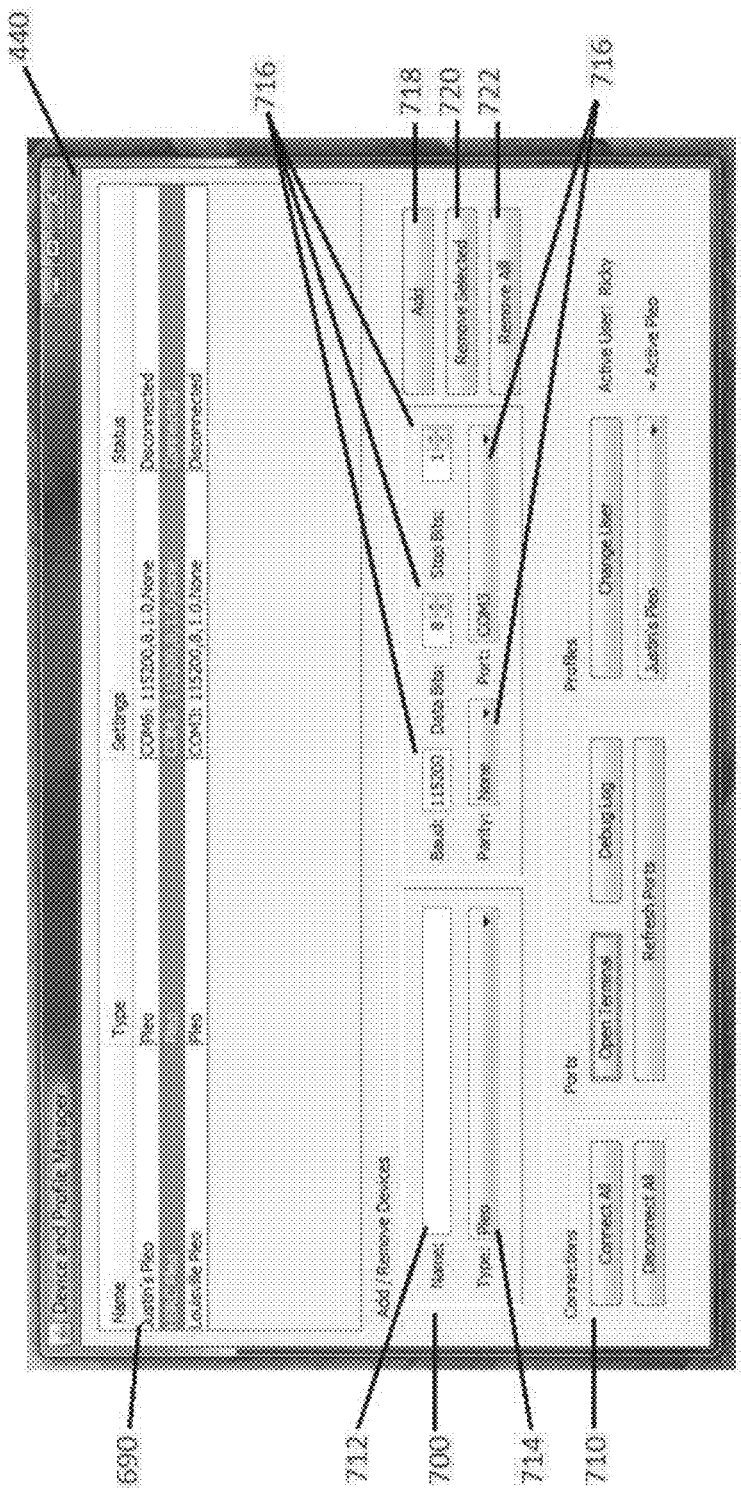
FIG. 8 shows a screenshot of an exemplary embodiment of a device manager frame.

In a preferred exemplary embodiment, the present system and method comprise a device manager application. In some exemplary embodiments, a device manager application is accessible through a device and profile manager frame. FIG. 8 shows a screenshot of an exemplary embodiment of a device and profile manager frame 440. As shown in FIG. 8, a device manager application frame 440 may comprise a listing of the serial device profiles 690 that are recognized by the computer program. This may be a listing of different social robots being utilized, but it may also include serial devices other than social robots. A serial device other than a social robot may comprise a wireless healthcare device. In some exemplary embodiments where a device manager comprises a listing of social robots recognized by the computer program, the device manager further comprises information pertaining to different applications that have been or are executing with those social robots.

When the present system and method comprises a device manager application, the device manager application may be utilized to add or remove the profile of a social robot. In some exemplary embodiments, a device manager application frame 440 is utilized to add or remove the profile of a social robot. In one exemplary embodiment, where the profile of a social robot is added via a device manager, the computer program may then be utilized to communicate with the newly added robot. There are numerous ways a social robot could be added via a device manager application. In a preferred exemplary embodiment, a device manager application frame 440 comprises an "Add/Remove Devices Panel" 700. As in the exemplary embodiment of FIG. 8, within the panel 700 there may be a name field 712 where a system user can enter the name—or other identifying information—of a social robot (or other device) to be added or removed. The panel 700 may also comprise a type field 714 where a user may specify what type of device is being added or removed (i.e., robot, wireless healthcare device, etc.). The Panel may further comprise setting fields 716 where a user could configure the settings of a robot or other device to be added. In some embodiments, where only one type of robot is being utilized, such as PLEO's that have all been programmed in the same fashion, it may be unnecessary for a system user to adjust the setting fields prior to adding a robot. An Add/Remove Devices panel of a device manager application frame 440 may further permit a system user to designate the COM port being utilized by a particular robot or device. An add/remove devices panel 700 may comprise an add button 718, remove selected button 720, and a remove all button 722. In some exemplary embodiments, a robot is added via a device manager application by a system user who has entered information into an add/remove devices panel 700 and has then electronically selected that the robot be added via the add button 718. Electronic selection could occur via the use of a mouse or another pointing device that is in communication with the computer. In some embodiments, a robot or device could be removed by a system user who has entered information into an add/remove devices panel 700 and has then electronically selected that the robot or device be removed via the remove selected button 720. In some exemplary embodiments, electronically selecting the remove all button 722 may cause all robots and devices that have been added into the system to be removed.

In one exemplary embodiment comprising a device manager application frame 440 that comprises a list of added robots, the profile of a robot can be removed when the system user selects/highlights the profile from the list and clicks on it with a pointing device and then selects the "remove selected" button. In an exemplary embodiment where the profile of a social robot has been removed via a device manager application, the removed robot is no longer in communication with the computer running the computer program. In some configurations where the system comprises a device manager application frame 440 that comprises an add/remove devices panel 700, the add/remove devices panel 700 can be utilized by a user of the system to both add and remove the profiles of robots. In other exemplary configurations, there are separate panels to be utilized by system users for adding and removing robot profiles from the system. A device and profile manager frame may further include a connections panel 710 for managing connections, ports, and user profiles.

In one exemplary embodiment, the present system and method comprises a device manager application that can be accessed by system users as a means of monitoring robots and other serial devices, but does not provide the means for adding and/or removing those devices. In this exemplary embodiment, the computer program may be configured to search for robots and serial devices that are turned on and within a certain range of the computer and automatically adds them. Similarly, the computer program may be configured to remove the robots and other serial devices when they have been turned off, moved outside of a certain range, etc. In another exemplary embodiment, the computer program is configured to allow system users to add and remove the profiles of robots and other serial devices, but the computer program is also configured to have the profiles added and removed by some other means.

Figure 9:
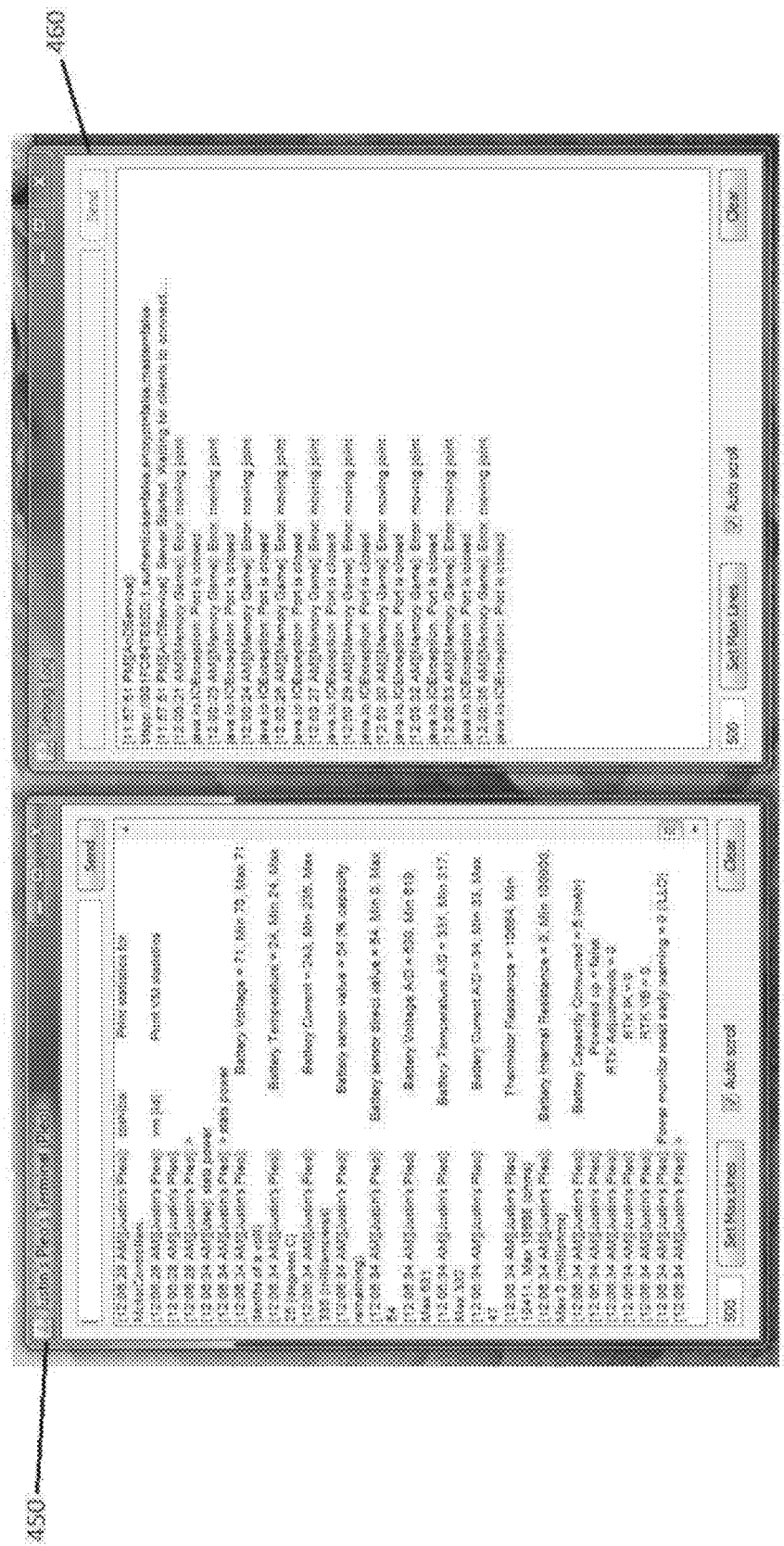
FIG. 9 shows a screenshot of an exemplary embodiment of terminals which may be utilized by the system and method of the present invention.

In exemplary embodiments comprising a device manager application, the device manager may provide direct access to the terminals of robots that have been added into the system. In some exemplary embodiments, a robot's terminal may be displayed by a robot terminal frame. A robot's terminal frame may contain information pertaining to that robot such as what applications have executed on the robot, the battery power available to the robot, readings that may have been taken by the robot, robot performance data, etc. In some embodiments, a device manager application may also provide access to a debug log. A debug log may be displayed in a debug log frame, but a debug log may also be generated in a manner that does not require a frame. For example, a debug log may be generated as an email message, word processing document, etc. In some exemplary embodiments, each robot that has been added into the system has its own debug log frame. In other exemplary embodiments, a single debug log frame may be utilized to show the debug log for all the robots of the system. In preferred exemplary embodiments, a debug log can be used to track any errors that may have been experienced by a robot. For example, a debug log for a single robot may display a list of all the times a system user attempted to run an application on the robot, but the application was unsuccessfully carried out by the robot. The debug log could also list any movement malfunctions experienced by a robot. In one exemplary embodiment, a debug log comprises much of the information a system user might need to determine whether or not a robot is functioning properly. There are many types of information that could be incorporated into a debug log of the present system and method. FIG. 9 shows a screenshot of an exemplary embodiment of a robot terminal frame 450 and an exemplary embodiment of a debug log frame 460.

An exemplary embodiment of a system and method for improving healthcare through social robotics may comprise an event scheduler application. An event scheduler application may enable a system user to schedule when a given robot is to perform certain functions for a patient. In some exemplary embodiments, the event scheduler application provides access to a daily schedule (i.e., regimen) for a patient. The daily schedule of a patient may comprise a list of events that are scheduled to play on that patient's robotic device during the day. When more than one robotic device is being utilized, a daily schedule may provide a list of events that are scheduled to play on all of the robots during a given day. In these exemplary embodiments, the schedule application may permit a single healthcare provider to assist in the care giving of multiple patients by coordinating the actions of numerous robots from a single computer.

In some exemplary embodiments, schedules may be available in time increments other than a 24 hour period such as schedules for a week, month, etc. In a preferred exemplary embodiment comprising an event scheduler application, a system user may access the application in order to choose from a list of pre-created schedules as well as to create new ones to suit their needs. Examples of events that may be scheduled via the event scheduler are skits, responsive skits, and memory games, but there are in fact many additional events that can be incorporated into a schedule of the present system and method.

Figure 5:
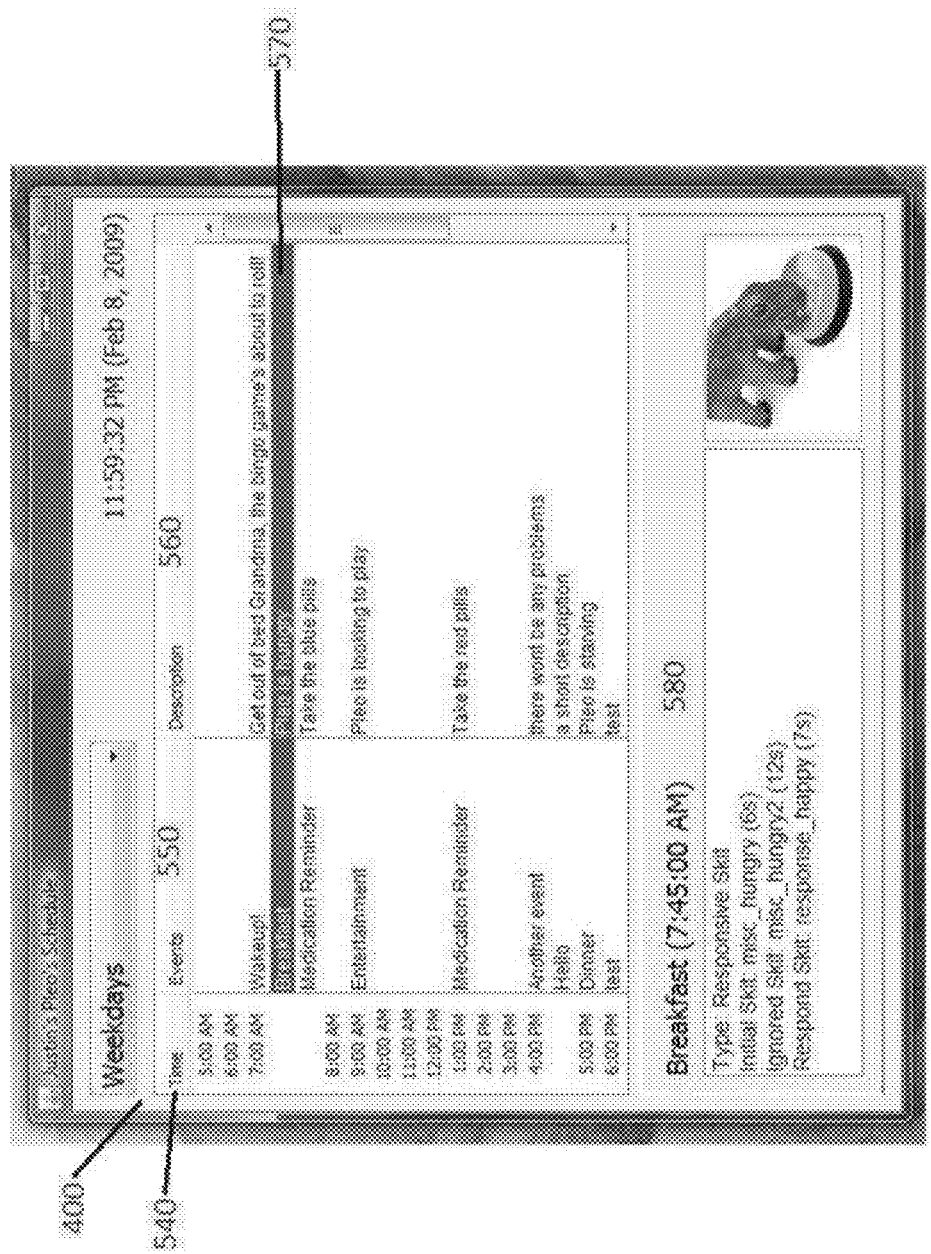
FIG. 5 shows a screenshot of an exemplary embodiment of a daily schedule frame that may be utilized by the system and method of the present invention.

An event scheduler application may be accessible through a daily schedule frame. FIG. 5 shows a screenshot of an exemplary embodiment of a daily schedule frame 400 of the present system and method. In a preferred exemplary embodiment, a daily schedule frame 400 can be opened by a user selecting the daily schedule application in the main frame 404. A daily schedule frame 400 may comprise a chart with a time column 540 an event column 550 and a description column 560. In such an exemplary embodiment, the time column 540 may display only times during which the robot is scheduled to perform an event, but in other exemplary embodiments the time column 540 may additionally display non-scheduled times. In a preferred exemplary embodiment, a time column 540 displays every hour for a specified time period (such as a day, half of a day, week, etc.). An event column 550 within a daily schedule main frame 400 may display a key word or key words for robot events that have been scheduled. Examples of some key words that may be displayed in an event column 550 are shown in FIG. 5 and include "wakeup", "breakfast", "medication reminder", "entertainment", etc. A description column 560 may be utilized to enter more detailed information concerning scheduled events.

In a preferred exemplary embodiment, a daily schedule frame 400 is interactive. An interactive daily schedule frame 400 may permit a user to alter already scheduled events, add scheduled events, remove scheduled events, etc. An interactive daily schedule frame 400 may permit a user to highlight scheduled events to review, amend, etc. details about the scheduled events. FIG. 5 shows an exemplary embodiment of an event having been selected with a highlight 570. When an event has been highlighted, the daily schedule frame 400 may present skit data details 580 for viewing.

In a preferred exemplary embodiment, the computer comprises a database. When the computer comprises a database, the database may be utilized for storing regimen data relating to a health activity of a patient or multiple patients. In preferred exemplary embodiments, the regimen data of a patient is entered through the scheduling frame of the system's scheduling application. Regimen data relating to a health activity of a patient may comprise a daily time at which the patient is supposed to take a measurement with a wireless healthcare device in communication with the computer. In other exemplary embodiments, regimen data may comprise a variety of times at which a patient is supposed to take a measurement with a wireless healthcare device in communication with the computer in which the variety of times are not necessarily a day apart. For example, a patient may need to measure his blood glucose levels after each meal. In other exemplary embodiments, regimen data may comprise health goal data, healthy measurement data for the patient, unhealthy measurement data for the patient, etc. For example, an overweight patient's regimen data may comprise daily weight goals that the patient is supposed to obtain to be successful in weight loss. In other examples, regimen data may comprise the blood glucose level a patient is supposed to maintain. There are numerous types of regimen data that may be stored in a database of the present invention.

In a preferred exemplary embodiment, a wireless healthcare device obtains data relating to a patient's health activity—such as weight recorded by a scale—and transmits the data to the computer. Upon receiving the data from the wireless healthcare device, the computer then accesses the database storing the regimen data that relates to the healthy activity and compares the received data with the stored regimen data. In the exemplary embodiment where the received data comprises weight data, the stored regimen data may comprise a goal weight. Upon making the comparison, the computer transmits a signal to the robot causing the robot to exhibit a certain behavior. The robot may be made to exhibit one response if the data received matches the stored regimen data and a second response if the data received from the wireless device does not match the regimen data.

In some exemplary embodiments, the system and method of the present invention comprise a computer program where the program comprises XML-formatted data. When the computer program comprises XML-formatted data, the system and method may further comprise an XML file loader. There are numerous types of file loaders that could be utilized.

In some exemplary embodiments, the system comprises a health graph. Examples of health graphs are a chart showing a patient's weight history, a graph of a patient's blood pressure readings taken over a certain period of time, a pie chart that shows a break-down of the nutrients that have been consumed by a patient, etc. A health graph of the system may be formulated by the computer program after it has obtained data from a wireless medical device. In another exemplary embodiment, a health graph may be formulated by the computer program after it has obtained data that has been input manually into the system by a system user. As an example of manual input, a system user could utilize a keyboard to enter health data into a computer which could then be transformed into a health graph. In another exemplary embodiment, a social robot sends a signal to a computer where the signal contains data that is utilized in forming a health graph. In some instances, the computer program may automatically generate a health graph upon the receipt of certain data. In other exemplary embodiments, a system user may be required to enter a command prior to the generation of the health graph. There are numerous ways the system and method of the present invention can comprise and generate a health graph.

Figure 4:
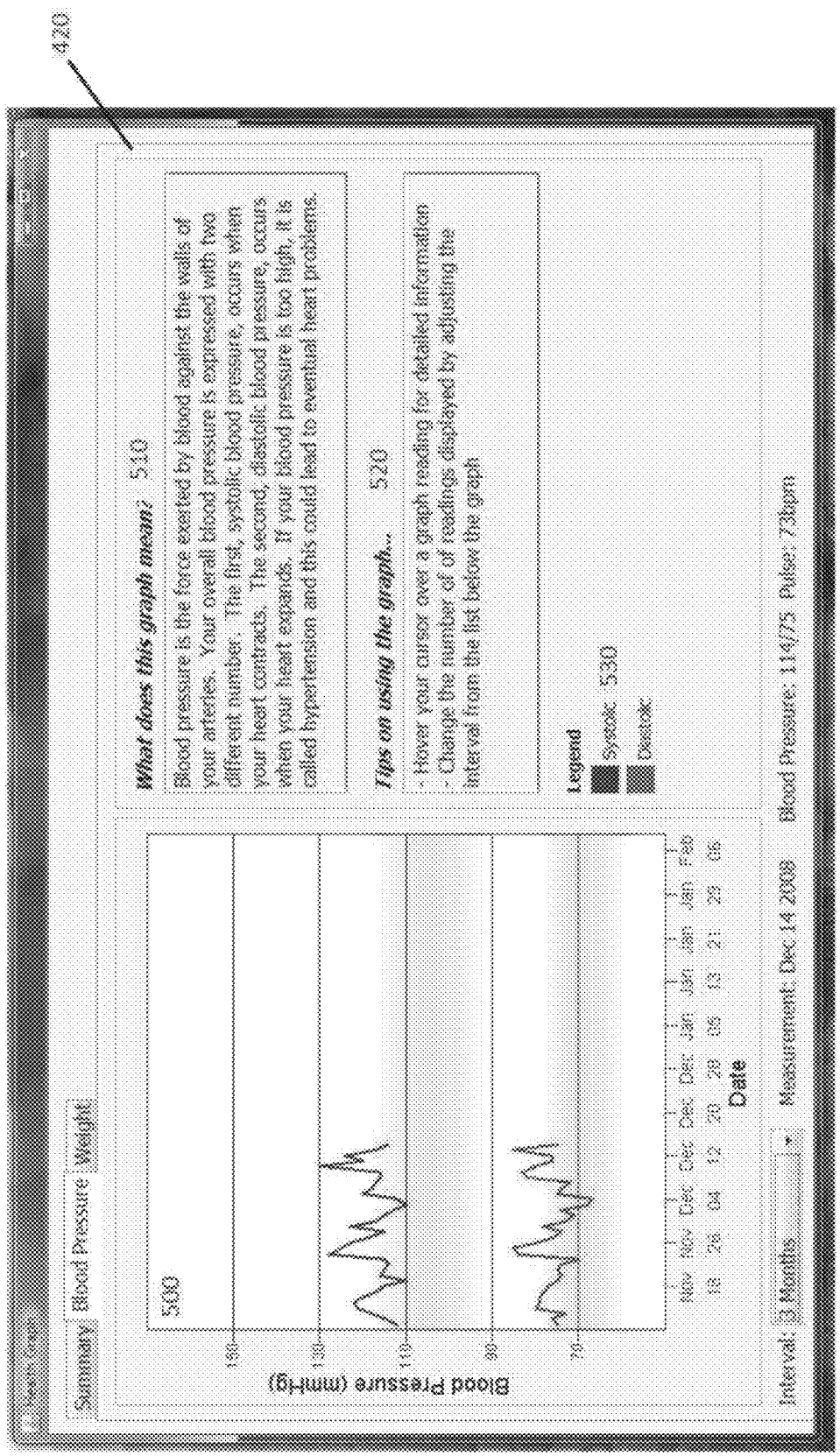
FIG. 4 shows a screenshot of an exemplary embodiment of a health graph frame which can be produced by the system and method of the present invention.

In a preferred exemplary embodiment, the system generates a health graph when a user selects a health graph application from the system's main frame 404. Selecting a health graph application from the main frame 404 may cause a health graph frame to be opened. When the system is able to generate more than one type of graph (i.e., graphs that represent different data sets), there may be separate applications for each graph type while in other exemplary embodiments a single application is utilized to generate more than one type of graph. In some exemplary embodiments comprising a health graph, the health graph is exhibited with accompanying information that explains what is being shown by the graph and may in some instances be accompanied by other information. FIG. 4 shows a screenshot of an exemplary embodiment of a health graph frame 420 of the present system where a graph 500 is exhibited with explanatory information 510 where the explanatory information explains what is being shown by the graph 500 and technical information 520 that explains how the graph 500 can be used. The exemplary health graph frame 420 of FIG. 4 additionally comprises a legend 530 for the graph 500.

A preferred exemplary embodiment of the present invention comprises a skit player application. A skit is defined as motions and sounds played together in a sequence. A skit player application may be utilized to play custom media through a social robot. In some exemplary embodiments, the application plays only skits that have been designed for the application. Skits may be utilized as the visual component of new healthcare examples. Some skits that may be implemented by the present system comprise a robot barking for attention, curling up and exhibiting signs of illness, exhibiting praise of a patient for following implementing a healthy habit, etc. In some exemplary embodiments comprising a skit player application, skits can be played by a social robot by opening the skit player application with the computer, electronically selecting the desired skit, and by electronically clicking the option to play the skit.

In some exemplary embodiments, a skit player application may be utilized to play responsive skits through a social robot. A responsive skit is an event which requires interaction from a system user. A responsive skit can sometimes demonstrate the introduction of new logic to a social robot without replacing its personality. The response component of a responsive skit can be triggered by accessory devices such as blood pressure cuffs, pill dispensers, floor sensors for kitchen, etc. in some exemplary embodiments. For example, the system may be programmed to remind a patient to take his or her blood pressure at 1:00 PM. Once the time of 1:00 PM is reached, the system can start to play a responsive skit through a social robot where the responsive skit is designed to attract the patient's attention. If the patient ignores the robot, the robot may exhibit a special skit to the patient to signify it is being ignored. The ignored skit may be demonstrated at certain time intervals until the patient has stopped ignoring the robot and has taken his or her blood pressure. Once the patient's blood pressure has been recorded, the social robot can exhibit certain responses based on the blood pressure of the patient. If the blood pressure is at a desired level, the robot can exhibit a response that it is pleased; if the blood pressure of the patient is unhealthy, the robot can act displeased by groaning, etc.

In some exemplary embodiments comprising a responsive skit, the responsive skit may comprise three components: an initial skit, an ignored skit, and a respond skit. Where a responsive skit comprises three components, the initial skit may be the skit played by the robot at the start of a responsive event in order to get the attention of a patient. The ignored skit can be the skit that is played by the robot repeatedly until the maximum number of repeats has been reached or until the software has received a response signal from a device. Finally, the respond skit may be the skit that is played by the robot once the software has received a signal from a supported device. In some exemplary embodiments, responsive skits comprise more or less than three components.

In exemplary embodiments comprising a skit player application and a responsive skit that comprises three components, a responsive skit may be played by accessing the skit player application, changing the mode to "responsive skit", choosing which skits should be played for the initial skit, the ignored skit, and the response skit, setting the time period the robot will wait between ignored skits, setting the maximum number of times the robot will play the ignored skit, and by electronically selecting play. In other exemplary embodiments, not all of these actions must be taken prior to the robot playing a responsive skit. For example, in some embodiments, multiple components of a responsive skit can be saved together so that a system user need only select the file relating to the particular skit which will then result in the playing of all desired components.

Figure 7:
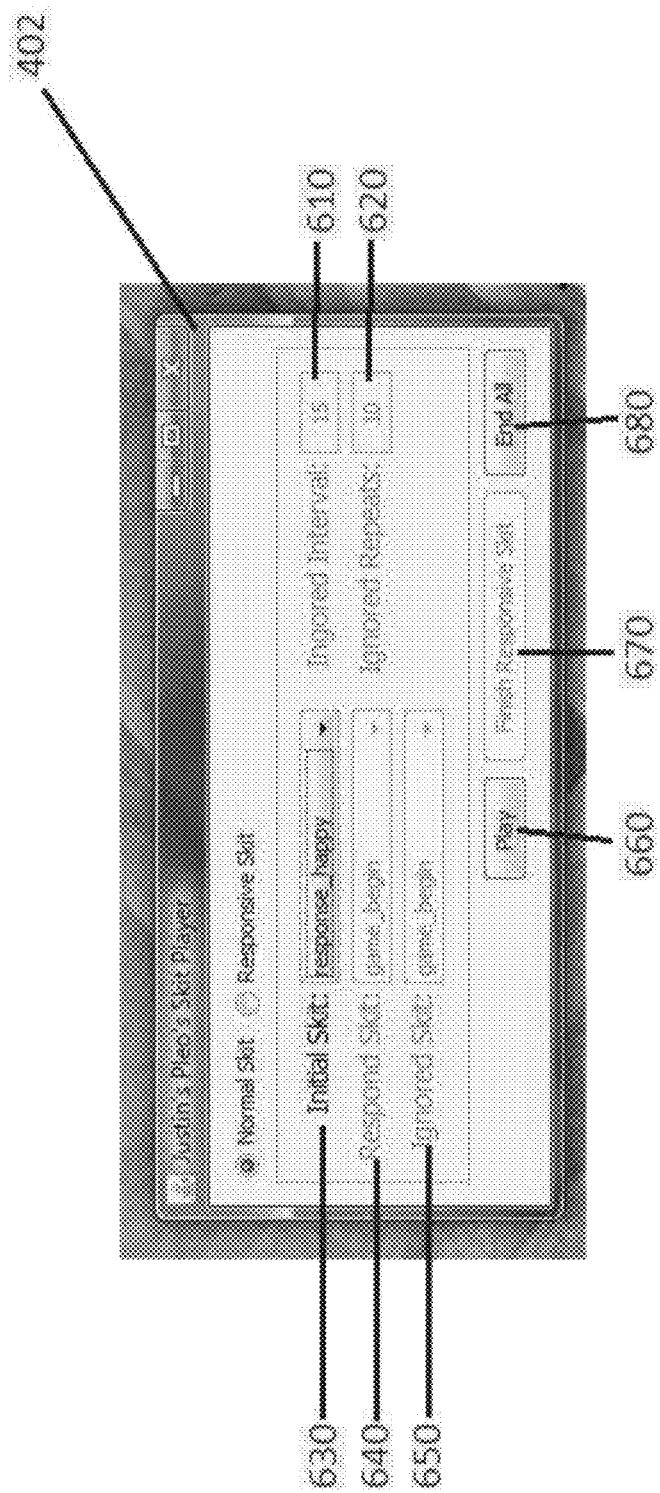
FIG. 7 shows a screenshot of an exemplary embodiment of a skit player frame.

In a preferred exemplary embodiment, a skit player application is accessible through a skit player frame. FIG. 7 shows a screen shot of an exemplary embodiment of a skit player frame 402 of an exemplary skit player application. In some exemplary embodiments comprising a skit player frame 402, the frame may be utilized to control the skits exhibited by a social robot. For example, the exemplary embodiment of FIG. 7 comprises an ignored interval data field 610 and an ignored repeat data field 620. These data fields may permit a user to control how long the robot waits before exhibiting an ignored skit and how many times an ignored skit will be exhibited respectively. A skit player frame may also comprise an initial skit field 630, a respond skit field 640, and an ignored skit field 650 which permit a user to select the type of skit a robot is to exhibit upon the occurrence of a certain event or at a certain time. A skit player frame 402 may also comprise a play button 660, a finish responsive skit button 670 and an end all button 680. In one exemplary embodiment, the type of skit entered into the initial skit field 630 may be the skit exhibited by the robot when a user selects the play button 660. In this example, if the patient does not respond to the exhibited initial skit, the robot exhibits the type of skit the user selected in the ignored skit field 650. The ignored skit may be exhibited at the interval that was entered into the ignored interval field 610 and for the number of times that the user entered into the ignored repeats field 620 unless the patient responds to the robot. Once the patient responds to the robot, the robot may exhibit the skit that was entered into the respond skit field 640. The finish responsive skit button 670 may be selected should the user wish to end the game early while the end all button 680 may be selected to end any of the exhibited skits being performed by the robot at any time.

In some exemplary embodiments, all skits to be played through a social robot are stored in a queue by the computer program. In these exemplary embodiments further comprising a skit player application, the skit player application may use the queue in conjunction with the daily schedule. For example, the daily schedule may indicate that a social robot is to play four different skits at certain times during the day. The event queue for that robot would then include those four skits. In some exemplary embodiments where all events to be performed by a social robot are saved as a queue by the computer, a system user cannot use the robot to play a skit that has not been included in the daily schedule until all the events already in the queue have been performed. In other exemplary embodiments, a system user may override a social robot's event queue. In embodiments where a system user may override a social robot's event queue, the overriding may take place by the electronic selection of an "end all" button contained in the skit player application.

Some exemplary embodiments will comprise more than one social robot. In exemplary embodiments comprising more than one robot as well as a skit player application, it may be necessary for a system user to indicate which robot a particular skit is to be played on. In other exemplary embodiments comprising more than one robot, when a computer receives a signal from an uploaded device, a responsive skit will be played on only a single robot that has been made active by the computer. It is also possible for a single signal from an uploaded device to trigger a responsive skit to be played by more than one robot.

In an exemplary embodiment, a social robot is capable of playing games with a system user. In a preferred embodiment, a robot plays games with a system user where the games are designed to encourage healthy behavior. An example of a game that could be played by a social robot with a system user is a memory game that is similar to Simon, a game where four panels light up and play sound in random sequences which the player must memorize. A social robot may comprise lights in order to create a memory game for a system user, but this is not necessary. Some social robots may utilize motion to play a memory game with a system user. For example, when it is the robot's turn, it could create a sequence of movements using its front legs, head, and/or tail and then when it is the user's turn, the user could attempt to recreate the robot's sequence by touching sensors that correspond to the robot's joints. In a preferred exemplary embodiment, the robot has a number of signaling members (such as lights) and a number of sensors where there is a sensor corresponding to each signaling member. When the signaling members comprise lights, the robot may play a memory game with a patient by exhibiting a sequence with its lights (i.e. by lighting and unlighting the lights in a pattern). The patient must then touch the robot's sensors in the same sequence. In a preferred exemplary embodiment, the sensor that corresponds to a given signaling member will be the sensor that is located the nearest to it. A signaling member could also be a moveable member of the robot such as a robotic arm, robotic leg, robotic tail, etc.

Figure 6:
FIG. 6 shows a screenshot of an exemplary embodiment of a game frame which may be utilized by the system and method of the present invention.

There are many different games that a social robot could play with a system user. When a social robot is capable of playing games with a system user, the computer program of the system may comprise a game module. The game module may be used to start a game with the social robot. In one exemplary embodiment, a game module is catered to a specific social robot. A game module may be utilized to start a game on numerous social robots at the same time. In one exemplary embodiment, a game frame provides access to a game module. FIG. 6 shows a screen shot of an exemplary embodiment of a game frame 430 of an exemplary game module. As shown, a game frame 430 may comprise a start button 590 and an end button 600 which permit a user to instruct a robot to begin and end playing a game with a patient. In a preferred exemplary embodiment, there are multiple ways a user may instruct a robot to begin and end playing a game with a patient. For example, a user may utilize the start button 590 and the end button 600 of a game frame 430 but he or she may also schedule the start and end of a game through the daily schedule frame 400. In some exemplary embodiments, there are multiple game frames representing different types of games the robot may play. In other exemplary embodiments, a single game frame 400 may be utilized for more than one type of game.

The exemplary embodiments herein disclosed are not intended to be exhaustive or to unnecessarily limit the scope of the invention. The exemplary embodiments disclosed were chosen and described in order to explain the principles of the invention so that others skilled in the art may practice the invention. Having shown and described exemplary embodiments of the invention, those skilled in the art will realize that many variations and modifications may be made to affect the described invention. Many of those variations and modifications will provide the same result and fall within the spirit of the claimed invention. It is the intention, therefore, to limit the invention only as indicated by the scope of the claims.

What is claimed is:

1. A system for improving the healthcare of a patient comprising:
   a programmable autonomous social robot configured to move in ways that give the appearance of various behaviors and emotional reactions and to play various sounds in sequence with said movements, said robot comprising a series of signaling devices and a series of corresponding touch sensors;
   a wireless healthcare device configured to receive data regarding one or more health activities performed by the patient using the wireless healthcare device; and
   a computer configured to receive data from the wireless healthcare device, said computer comprising data representing healthcare goals for the one or more health activities, a schedule for performing the one or more health activities, and executable software instructions, which when executed configure the robot to:
      perform a positive emotional reaction skit when data received from the wireless healthcare device indicates progress towards the respective health goal, and
      perform a negative emotional reaction skit when data received from the wireless healthcare device indicates regression from the respective health goal.

2. The system of claim 1 further comprising:
   memory game software instructions stored at the computer, which when executed configure the robot to:
      actuate one or more of the signaling devices in a programmed sequence,
      monitor for a user sequence of triggered touch sensors in response to the programmed sequence,
      receive the user sequence from the robot, and
      compare the user sequence to the programmed sequence to determine if there is a match.

3. The system of claim 1 wherein:
   the robot has the appearance of a non-human animal.

4. The system of claim 1 wherein:
   the health activity is selected from the group consisting of: measuring the patient's weight, measuring the patient's blood pressure, measuring the patient's temperature, measuring the patient's glucose, and measuring the patient's pulse.

5. The system of claim 4 wherein:
   the wireless healthcare device is selected from the group consisting of: a scale, a blood pressure cuff, a thermometer, a glucose meter, a pulse meter, and a urinalysis device.

6. The system of claim 1 wherein:
   said software instructions, when executed, configure the robot to:
      move in ways which give the appearance of relief or pleasure as well as play particular sounds in sequence with said movements when performing said positive emotional reaction skit; and
      move in ways which give the appearance of disappointment as well as play particular sounds in sequence with said movements when performing said negative emotional reaction skit.

7. The system of claim 1 further comprising:
   additional skit software instructions stored at the computer, which when executed configure the robot to:
      perform an attention skit if a scheduled health activity is not performed when scheduled,
      wait a predetermined amount of time, and
      perform an ignored skit if a scheduled health activity is not performed after the predetermined amount of time.

8. The system of claim 7 wherein:
   said additional software instructions, when executed, configure the robot to:
      move in ways which give the appearance of anxiety as well as play particular sounds in sequence with said movements when performing said attention skit; and
      move in ways which give the appearance of hunger or illness as well as play particular sounds in sequence with said movements when performing said ignored skit.

9. The system of claim 1 wherein:
   the computer is located at the robot.

10. The system of claim 1 wherein:
    the computer is located remote from the robot and communicates wirelessly with the robot.

11. The system of claim 1 further comprising:
    a display in electronic communication with the computer for displaying a graph of the health activity data over a period of time.

12. The system of claim 1 wherein:
    the signaling devices comprise lights; and
    actuation of the signaling devices causes the respective signaling device to be illuminated.

13. The system of claim 12 wherein:
    the signaling devices comprise appendages of the robot; and
    actuation of the signaling devices causes the respective appendage to move.

14. A system for improving the healthcare of a patient comprising:
    a programmable social robot having the appearance of a non-human animal, wherein the robot is configured to move in ways that give the appearance of various behaviors and emotional reactions;
    a wireless healthcare device configured to receive data regarding one or more health activities performed by the patient using the wireless healthcare device; and
    a computer configured to receive data from the wireless healthcare device, said computer comprising data representing healthcare goals for the one or more health activities, a schedule for performing the one or more health activities, and executable software instructions, which when executed configure the robot to:

perform a positive emotional reaction skit configured to reflect an appearance of pleasure or relief when data received from the wireless healthcare device indicates progress towards the respective health goal, perform a negative emotional reaction skit configured to reflect an appearance of disappointment when data received from the wireless healthcare device indicates regression from the respective health goal, perform an attention skit configured to reflect an appearance of anxiety if a scheduled health activity is not performed when scheduled, and perform an ignored skit configured to reflect an appearance of hunger or illness if the scheduled health activity is not performed after waiting a predetermined amount of time following performance of the attention skit.

15. The system of claim 14 further comprising:
a plurality of signaling devices located on the robot; and
a plurality of touch sensors located on the robot to correspond with each of said signaling devices.

16. The system of claim 15 further comprising:
memory game software instructions stored at the computer, which when executed configure the robot to:
actuate one or more of the signaling devices in a first sequence,
monitor for a user sequence of triggered touch sensors in response to the actuation of the signalizing devices in the first sequence,
receive the user sequence from the robot, and
compare the user sequence to the first sequence to determine if there is a match.

17. The system of claim 14 wherein:
the health activity is selected from the group consisting of: measuring the patient's weight, measuring the patient's blood pressure, measuring the patient's temperature, measuring the patient's glucose, and measuring the patient's pulse; and
the wireless healthcare device is selected from the group consisting of: a scale, a blood pressure cuff, a thermometer, a glucose meter, a pulse meter, and a urinalysis device.

18. The system of claim 1 wherein:
the computer is located remote from the robot and communicates wirelessly with the robot.

19. The system of claim 14 wherein:
said software instructions, when executed, configure the robot to play particular sounds in sequence with the movements of each of said positive emotional reaction skit, said negative emotional reactions kit, said attention skit, and said ignored skit.

20. A system for improving the healthcare of a patient comprising:
a programmable social robot having the appearance of a non-human animal, wherein the robot is configured to move in ways that give the appearance of various emotional reactions, said robot comprising a number of lights and a number of touch sensors;
a wireless healthcare device configured to receive data regarding one or more health activities performed by the patient; and
a computer configured to receive data from the wireless healthcare device, and store data representing healthcare goals for the one or more health activities, and a schedule for performing the one or more health activities;
said computer further including executable software instructions, which when executed direct the robot to:
perform a positive reaction when data received from the wireless healthcare device indicates progress towards the respective health goal,
perform a negative reaction when data received from the wireless healthcare device indicates regression from the respective health goal,
perform an attention reaction if a scheduled health activity is not performed when scheduled, and
perform a memory game by:
actuating lights in a first sequence,
monitoring for a user sequence of triggered touch sensors in response to the first sequence,
receiving the user sequence from the robot, and
comparing the user sequence to the first sequence to determine if there is a match.

* * * * *